(12) United States Patent
Stasiak

(10) Patent No.: US 6,261,095 B1
(45) Date of Patent: Jul. 17, 2001

(54) DENTAL TOOL FOR TOOTH RESTORATION

(76) Inventor: Thaddeus Stasiak, One Northgate Sq., Greensburg, PA (US) 15601

( * ) Notice: Subject to any disclaimer, the term of this patent is extended or adjusted under 35 U.S.C. 154(b) by 0 days.

(21) Appl. No.: 09/455,071

(22) Filed: Dec. 6, 1999

(51) Int. Cl.[7] ....................................................... A61C 5/04
(52) U.S. Cl. ............................ 433/155; 433/153; 433/161
(58) Field of Search ................................... 433/155, 156, 433/157, 158, 150, 153, 152, 136, 139, 94, 161, 163

(56) References Cited

U.S. PATENT DOCUMENTS

| | | | |
|---|---|---|---|
| 1,106,815 | * | 8/1914 | Hopkins ................................ 433/153 |
| 1,990,889 | * | 2/1935 | Bandman ............................. 433/153 |
| 4,758,159 | * | 7/1988 | Weissman ............................ 433/161 |

* cited by examiner

Primary Examiner—John J. Wilson
Assistant Examiner—Melba Bumgarner
(74) Attorney, Agent, or Firm—Kevin J. Garber

(57) ABSTRACT jIn restoration of teeth, the use of conventional matrix bands and wedges tends to leave gaps or spaces which can through inefficient restoration lead to fracture or infection, and also prove to be time consuming and inefficient. This invention addresses shortcomings of conventional restorative devices by providing an easy to use dental tool that has a first member and a second member with struts that adjust to fit into the proximal box, and that provides a predictably tight contact area for optimal tooth restoration.

10 Claims, 4 Drawing Sheets

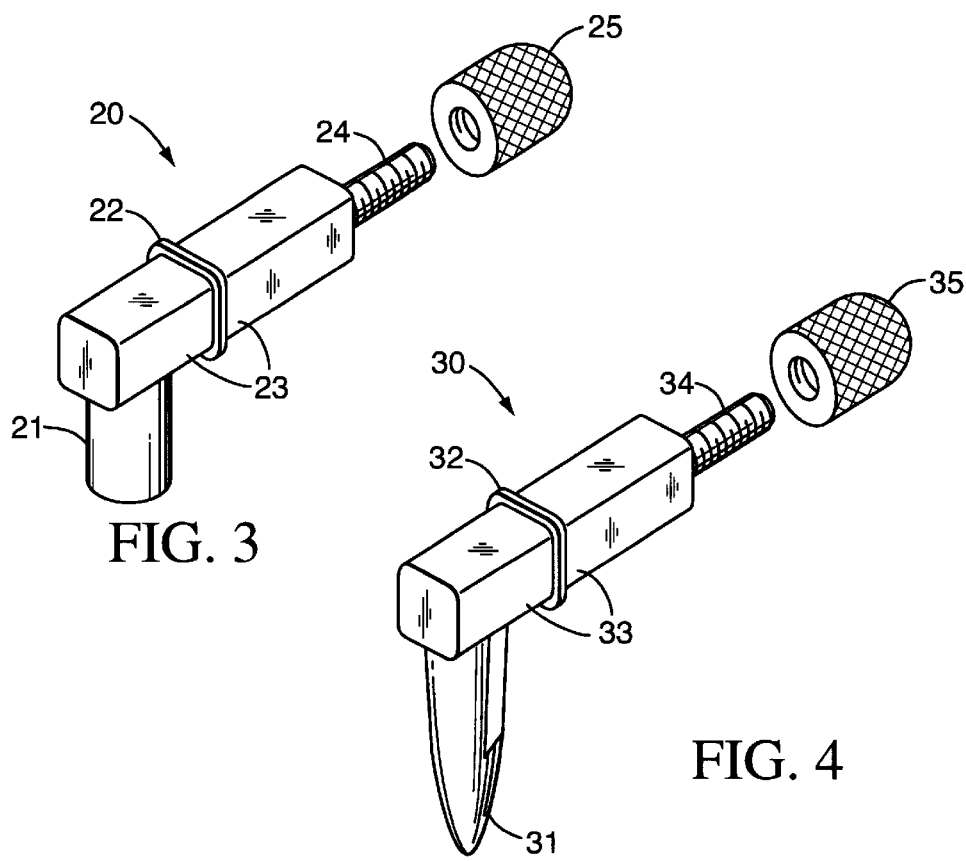
FIG. 3
FIG. 4
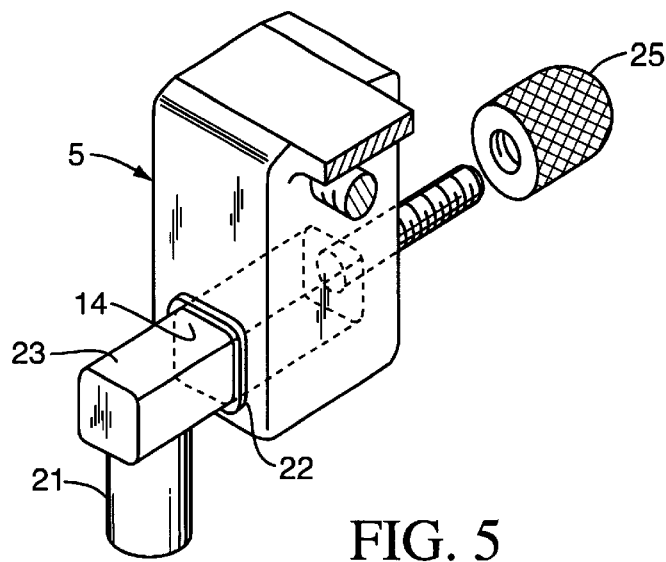
FIG. 5

DENTAL TOOL FOR TOOTH RESTORATION

TECHNICAL FIELD

This invention relates to the restoration of teeth to their normal, anatomical form and function, particularly to a device for facilitating restoration with the use of conventional matrix bands, and more particularly, to the repair of interproximal caries using light cured composite materials.

BACKGROUND OF THE INVENTION

Anatomically, teeth are aligned to and with each other in an arch form contacting each other on a mesial and distal side. The size, shape and tightness of these contacts is vital to the health of the teeth and supporting periodontal structures. As caries develop in the interproximal surfaces, there is a need to restore the surfaces to the proper anatomical form and to reestablish the appropriate contact points.

The typical practice, following cavity preparation, is to place a dental matrix band circumferentially around a tooth for filling and holding restorative material to achieve the proper contour. Dentists commonly use the dental matrix band with a matrix band retainer instrument which helps to position the band and to tighten it securely about the tooth. To adjust the fit of the band and to maintain it in a suitable position during restoration, other dental instruments, such as the triangular shaped wedge, are commonly used. The wedge may be inserted, just above the gumline, between the tooth being restored and an adjacent tooth. The wedge slightly separates the teeth to accommodate the thickness of the band and to create a seal at the end of the band to keep the filling material in place. It is also known in the art to use a sectional matrix ring system which fits between two teeth for applying contoured bands and establishing a tight contact.

Over the years, various types of devices have been developed to help distend the band during an initial composite curing period. While the conventional devices have added many advances to the field, they retain significant limitations. Perhaps the most common limitation of conventional devices is that the restoration tends to result with a narrow contact area at the marginal ridge. When the contact area is smaller in size than ideal, the restoration is weak and subject to fracture. It can leave a gap between the contact point, gum and neighboring teeth for food entrapment and infection. Devices designed to overcome contact weakness have been shown to be cumbersome in use and to provide inconsistent results. The wedge, for instance, is operated by hand and thus depends upon a variant level of torque which can be subject to human error. Once in position, the wedge can shift out of place. If made of wood, or similar porous material, it is prone to moisten with saliva and lose its effectiveness. The matrix ring instrument requires an ideal preparation to function correctly and tends to be cumbersome due to the need to engage multiple components. These devices can be cumbersome, time consuming and may even hinder the practitioners' view of the restoration.

In the past, the most common restorative material has been silver amalgam, a metal putty. Due to its strength, amalgam material maintains its shape. In this way, the amalgam filling material also functions to assist with the displacement of the dental matrix band into tight contact with the adjacent tooth. Today, with the advancements in dental materials, compactable composite resins are increasingly used. Unlike amalgams, composite resins do not have the condenseability necessary to displace the matrix band in position during restoration. As a result, the elastic memory of the band pulls away from the adjacent tooth thereby leaving a gap or space. The elastic memory exhibits a very flat proximal surface which, following restoration, yields a thin contact area at the marginal ridge. This result is clinically undesirable. The band is not well deformed to appropriate contour by composite material alone.

SUMMARY OF THE INVENTION

This invention facilitates the restoration of teeth by providing for deformation of the interproximal segments(s) of a matrix band, or other dental aid, to the natural tooth contours through a predictable tight contact area with an easy-to-use self-supporting tool. It can be easily and optimally used in conjunction with conventional devices, such as wedges. This invention adapts for use on many types of preparations. It further allows for the use of cured composite resin materials, and is designed to provide maximal visibility and access for quick deposition and curing of the materials.

The invention is a dental tool for assisting the restoration of a tooth, comprising, as a preferred embodiment, an elongated frame, having a first member at one end of the elongated frame, the first member having a channel for receiving a strut component; a second member movably attached to the elongated frame parallel to the first member, the second member also having a channel for receiving a strut component; a means for adjusting the second member relative to the first member connected with the second member and attached to the elongated frame opposite to the first member; and strut components removably disposed through the channels of the first and second members. The strut components can include struts extending perpendicularly therefrom and a means for removably attaching the strut components to the members. Optionally, one strut is symmetrically conical in shape with a curved base and a flattened part for optimal contact with the tooth, and another strut is shorter, cylindrical in shape and has a flattened end to provide counter pressure.

The invention accommodates variations in tooth sizes by providing a means for adjusting the members to alter the distance between the struts. Depending upon the type of restoration desired, struts of varied length and size can be used. They can be removed and reattached in an inverted position for use of the invention on a tooth in the opposite side of the mouth.

BRIEF DESCRIPTION OF THE DRAWINGS

FIG. 3 shows an embodiment of a strut component with a cylindrical strut.

FIG. 4 shows an embodiment of a strut component with a symmetrical conical strut.

FIG. 5 shows a preferred embodiment of attaching a strut component to the first member.

DETAILED DESCRIPTION OF THE INVENTION

Figure 1:
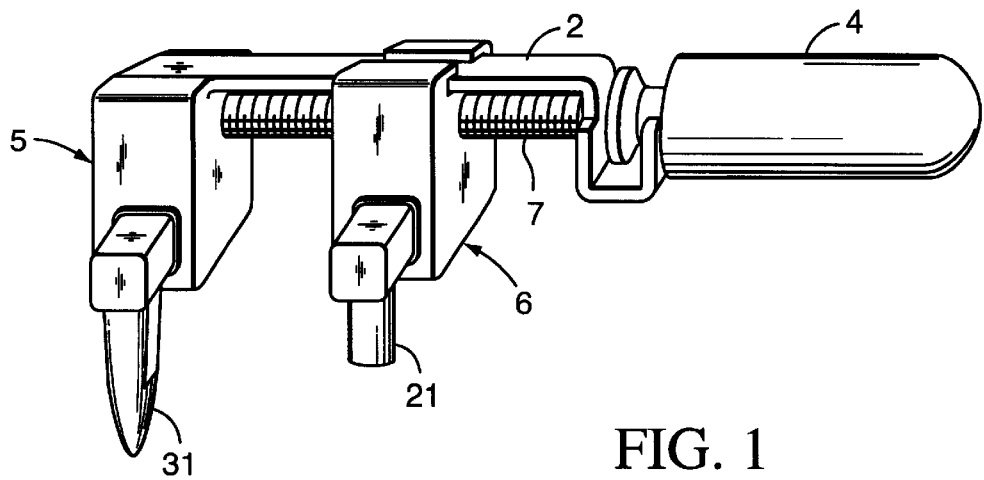
FIG. 1 is a side view illustrating a preferred embodiment of the dental tool.
Figure 2:
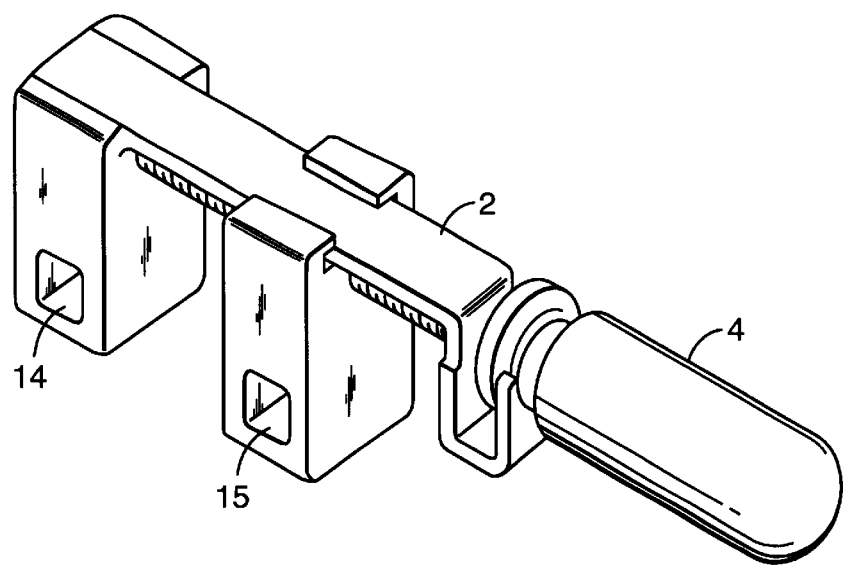
FIG. 2 is a top view of the dental tool showing channels to receive strut components.

Referring now to the drawings, and particularly to FIGS. 1 and 2, an embodiment of the dental tool invention is shown generally 1 and includes an elongated frame 2, a first member 5, a second member 6 that is parallel to the first member 5, and a means for adjusting the first 5 and second 6 members relative to one another in order to tighten a matrix band or other dental aid about a tooth. Each of said first member 5 and second member 6 has a strut extending therefrom for making contact with the tooth. In a preferred embodiment of the invention, each of said first member 5 and second member 6 has a channel 14 and 15, respectively, disposed through it for receiving a strut component, as shown in FIG. 2. Elongated frame 2 preferably has the first member 5 nonmovably fixed to one end of elongated frame 2 and has second member 6 movably attached to elongated frame 2, as depicted in FIGS. 1 and 2. However, it is possible to nonmovably affix second member 6 to elongated frame 2 and to movably attach first member 5 to elongated frame 2, or to movably attach both first member 5 and second member 6 to elongated frame 2, and still attain the same result with the invention. The means for adjusting second member 6 relative to first member 5 preferably is a handle 4 with a helical thread stem 7 extending therefrom that is attached to elongated frame 2 at its end opposite first member 5 and that is disposed through second member 6 and into first member 5. The practitioner may turn handle 4 with his or her fingers, thereby advancing or retreating second member 6 along helical thread 7 toward or away from first member 5. This allows the tool to tighten or release a matrix band or other dental aid as desired.

In a preferred embodiment, as shown in FIG. 2, the first member 5 and second member 6 have channels 14 and 15, respectively, disposed through them for receiving strut components 20 or 30. However, it is possible to have the first member 5 and second member 6 formed into struts, rather than using strut components 20 and 30, and still attain the same result with the invention. As shown in FIG. 3, strut component 20 is comprised of strut 21 extending perpendicularly from strut component 20, of ridge 22, of body 23 adapted to be received by channel 14 or 15, and of a means for removably attaching strut component 21 to first member 5 or second member 6 as desired. In a preferred embodiment, the means for removably attaching strut component 20 includes threaded portion 24 and a removable cap 25 designed to receive said portion 24 as shown in FIG. 3. Strut 21 is generally cylindrical in shape in proportion to a tooth and has a flattened end to provide a point of counter pressure on the tooth. Ridge 22 is slightly raised relative to the body 23 of the strut component. Body 23 fits within channel 14 or 15 of first member 5 and/or second member 6, as desired, and ridge 22 serves to position strut component 20 within channel 14 or 15 and to align strut 21 properly with respect to dental tool 1. FIG. 5 shows how strut component 20 removably attaches to either first member 5 or second member 6.

As shown in FIG. 4, strut component 30 is comprised of strut 31 extending perpendicularly from strut component 30, of ridge 32, of body 33 adapted to be received by channel 14 or 15, and of a means for removably attaching strut component 31 to first member 5 or second member 6 as desired. In a preferred embodiment, the means for removably attaching strut component 30 includes threaded portion 34 and a removable cap 35 designed to receive said portion as shown in FIG. 4. Strut 31 is generally conical. It is generally symmetrically conical in shape in proportion to a tooth, with a flat part to contact the area being restored, and a curvature toward the gingival margin. Strut 31 is longer than strut 21 in order to properly distend a matrix band, which is fitted around the treated tooth, snugly against a neighboring tooth. Ridge 32 is slightly raised relative to the body 33 of the strut component. Body 33 fits within channel 14 or 15 of first member 5 and/or second member 6, as desired, and ridge 32 serves to position strut component 30 within channel 14 or 15 and to align strut 31 properly with respect to dental tool 1.

In this way, struts are easily adjusted or exchanged to suit the restoration by simply attaching or removing the strut component from the first member 5 and second member 6. Strut components 20 and 30 can be used interchangeably when placed on first member 5 and second member 6 for adapting the dental tool for use with a tooth on the opposite side of the mouth. The strut components 20 and 30 may be comprised of various materials including, for example, metal, nylon, polytetraflouride, polyethylene or quartz, among other materials.

Figure 6:
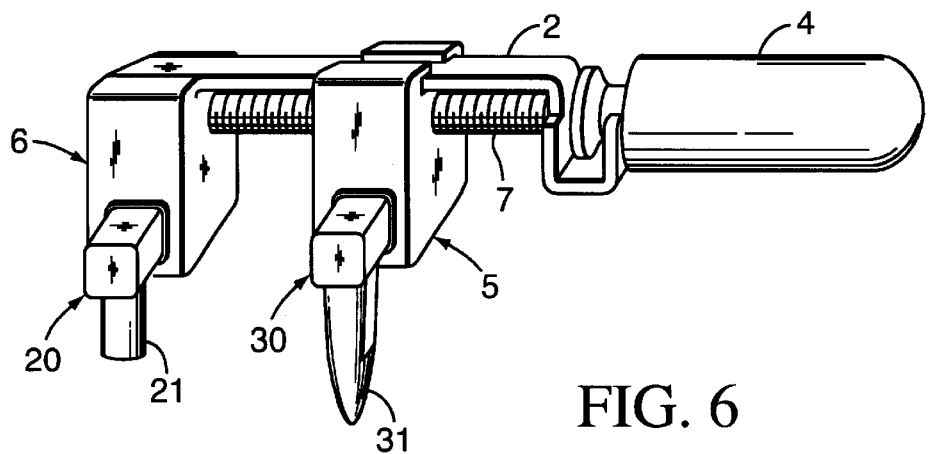
FIG. 6 shows an embodiment of the invention with struts of variant lengths.
Figure 7:
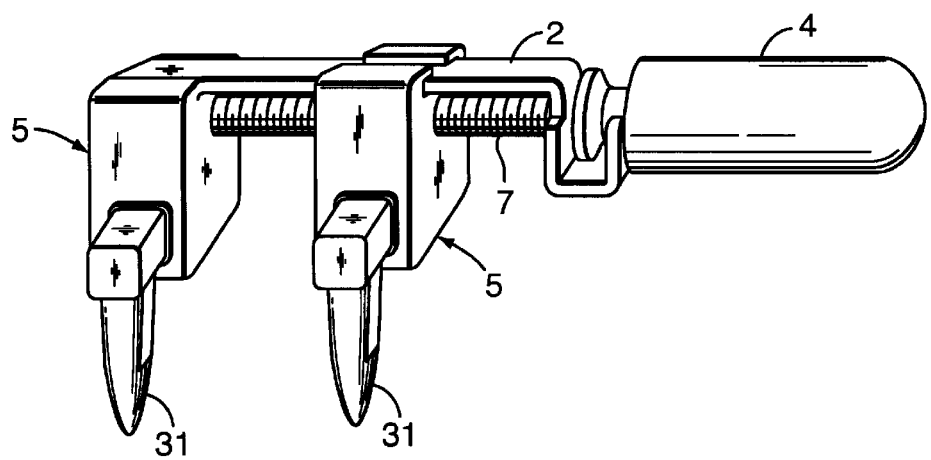
FIG. 7 shows an embodiment of the invention with struts of the same length.
Figure 8A:
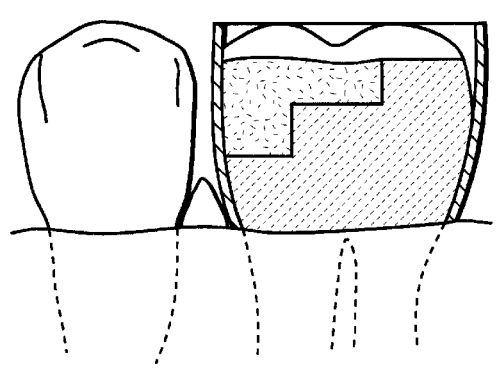
FIGS. 8A, 8B, 8C, and 8D show a use of the dental tool to aid in tooth restoration.
Figure 8B:
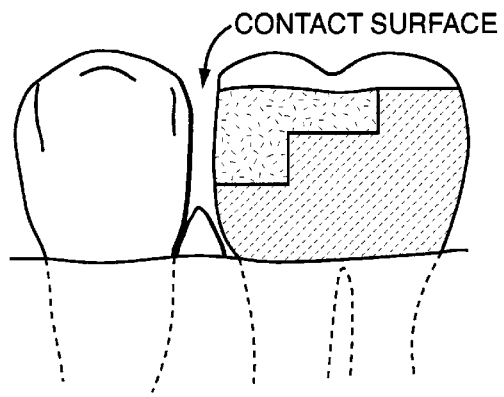
Figure 8C:
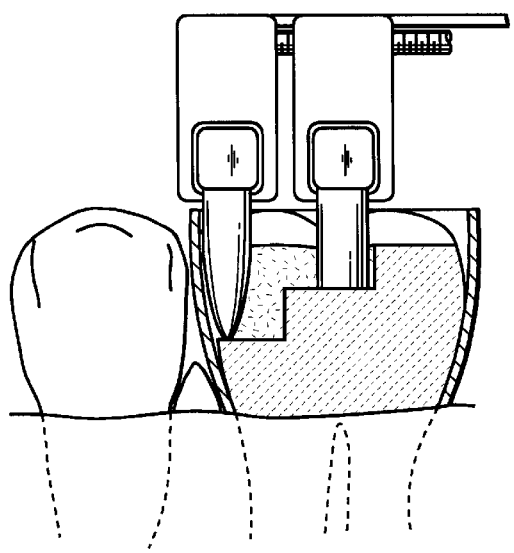
Figure 8D:
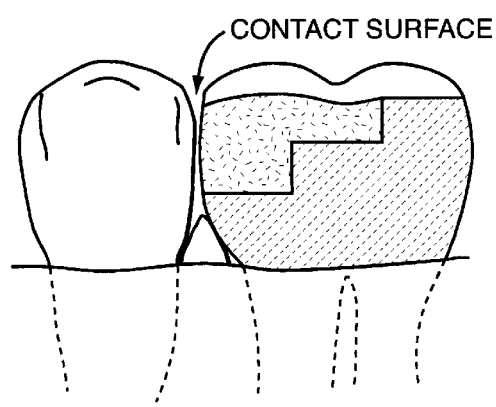

It should be noted that the dental tool can utilize strut component 30 on first member 5 and second member 6 so that a practitioner can use struts of the same size and shape, as shown in FIG. 7. Likewise, strut component 20 can be used on first member 5 and second member 6 at the same time. Alternatively, the practitioner can use the tool with strut components 30 and 20 when struts of unlike size and shape are desired, as shown in FIG. 6. Additionally, in this way, the struts 21 and 31 are offset in order to maximize vision. They are interchangeable and can be used in any combination to best advantage.

During use of the invention, the practitioner prepares the cavity by conventional or other means, extending to one or more interproximal surfaces, and removing all carious dentin. Unlike most other contact instruments, an intact axial wall is not needed to secure a tight contact. And, cavo-surface margins need not be in ideal positions. The matrix band is then placed, tightened and secured with a wedging device, and proper etching and bonding steps are begun. As this procedure sets, a small amount of composite is placed at the gingival floor(s) and this dental tool invention 1 is inserted. The dental tool 1 will distend and maintain proper band conformation by placing the strut components 20 and 30 in position relative to the preparation and by adjusting the strut components 20 and 30 as desired using the means for adjusting first member 5 and second member 6 relative to one another. Additional material, such as composite resin, is placed and cured to achieve a secure hold. Once cured, the dental tool invention 1 is removed and the remainder of the cavity is filled. The band and wedge are removed and the restoration, if desired, is adjusted and polished.

For a mesial occlusal or a distal occlusal, one strut, preferably conical strut 31, is placed into the proximal box and another strut, preferably short cylindrical strut 21, is placed at the pulpal floor in the dovetail section of the prepared cavity for counter pressure. For optimal advantage, the flattened portion of conical strut 31 is placed against the dental matrix band at the position of desired contact. Then, the handle 4 is adjusted to distend and shape the dental matrix band simultaneously achieving separation between the adjacent teeth, to account for the thickness of the matrix band. At this point, additional composite material can be placed and light cured. When sufficient material has been applied to maintain the generated tooth shape, form and contact area, the dental tool instrument is removed. Any residual voids are quickly filled, shaped, and cured. The wedge and band are removed and the restoration is adjusted, contoured and polished accordingly. FIGS. 8A through 8D show an illustration of how the invention can be used to improve tooth restoration, in contrast to a restoration done without the invention. The final filling is ideal in all aspects of anatomy, function, and contact—all with the use of readily available, recognizable, existing materials and supplies.

When the restoration involves both interproximal areas, or a mesial occlusal distal, another embodiment of the invention is shown to use a conical strut 31 on both first member 5 and second member 6. As described in the above embodiment, a small amount of restorative is placed at the gingival floor and, then, both struts are placed at ideal levels and tightened to conform the matrix band appropriately. Composite resin material is placed and cured until sufficient filling exists to hold the proper share without the apparatus. The invention is removed, voids filled, and the restoration is finished. With the extended depth of cure of the compactable resins now available, this procedure is very quick as well as predictably functional.

What is claimed is:

1. A dental tool for assisting the restoration of a tooth, comprising (a) an elongated frame having a first member at one end of said elongated frame, said first member having a channel for receiving a strut component; (b) a second member movably attached to said elongated frame parallel to said first member, said second member also having a channel for receiving a strut component; (c) a means for adjusting said second member relative to said first member connected with said second member and attached to said elongated frame opposite to said first member; and (d) strut components removably disposed through the channel of said first member and said second member.

2. A dental tool as set forth in claim 1, wherein said means for adjusting comprises a handle attached at one end of said elongated frame and a helical thread stem attached to said handle and disposed along said elongated frame through said second member and into said first member.

3. A dental tool as set forth in claim 1, wherein each said strut component has a strut extending perpendicularly therefrom, a ridge, a body adapted to be received by the channels of said first and second members, and a means for removably attaching to said first member and second member.

4. A dental tool as set forth in claim 3, wherein said means for removably attaching includes a threaded portion and a removable cap designed to receive said threaded portion.

5. A dental tool as set forth in claim 3, wherein at least one said strut is generally symmetrically conical in shape, and has a curved base and a flattened area to contact the tooth.

6. A dental tool as set forth in claim 3, wherein at least one said strut is generally cylindrical in shape and has a flattened end.

7. A dental tool as set forth in claim 3, wherein one said strut is generally conical in shape, and has a curved side and a flattened area to contact the tooth, and another strut is generally cylindrical and short relative to said contact strut.

8. A dental tool for assisting the restoration of a tooth, comprising (a) an elongated frame having a first member at one end of said elongated frame, said first member having a channel for receiving a strut component; (b) a second member movably attached to said elongated frame parallel to said first member, said second member also having a channel for receiving a strut component; (c) a handle with a helical thread stem attached to said elongated frame opposite to said first member, said helical thread disposed through said second member into said first member; (d) strut components removably disposed through the channel of said first member and said second member; and (e) a cylindrical strut attached to each of said strut components.

9. A dental tool for assisting the restoration of a tooth, comprising (a) an elongated frame having a first member at one end of said elongated frame, said first member having a channel for receiving a strut component; (b) a second member movably attached to said elongated frame parallel to said first member, said second member also having a channel for receiving a strut component; (c) a handle with a helical thread stem attached to said elongated frame opposite to said first member, said helical thread disposed through said second member into said first member; (d) strut components removably disposed through the channel of said first member and said second member; and (e) a symmetrically conical strut attached to each of said strut components.

10. A dental tool for assisting the restoration of a tooth, comprising (a) an elongated frame having a first member at one end of said elongated frame, said first member having a channel for receiving a strut component; (b) a second member movably attached to said elongated frame parallel to said first member, said second member also having a channel for receiving a strut component; (c) a handle with a helical thread stem attached to said elongated frame opposite to said first member, said helical thread disposed through said second member into said first member; (d) strut components removably disposed through the channel of said first member and said second member; and (e) a cylindrical strut attached to one of said strut components and a symmetrically conical strut attached to the other of said strut components.

\* \* \* \* \*